US012788878B2

(12) United States Patent
Callahan et al.

(10) Patent No.: US 12,788,878 B2
(45) Date of Patent: Nov. 10, 2026

(54) ACTIVATABLE MEDICAMENT DELIVERY CONTAINERS AND ASSEMBLIES

(71) Applicant: CareFusion 303, Inc., San Diego, CA (US)

(72) Inventors: Ryan Callahan, Long Beach, CA (US); George Mansour, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 967 days.

(21) Appl. No.: 17/950,856

(22) Filed: Sep. 22, 2022

(65) Prior Publication Data

US 2024/0100250 A1 Mar. 28, 2024

(51) Int. Cl.
*A61M 5/145* (2006.01)
*A61M 5/14* (2006.01)

(52) U.S. Cl.
CPC ...... *A61M 5/14586* (2013.01); *A61M 5/1413* (2013.01)

(58) Field of Classification Search
CPC .......... A61M 5/14244; A61M 5/14568; A61M 5/14593; B65D 83/673; B05B 11/025
See application file for complete search history.

(56) References Cited

U.S. PATENT DOCUMENTS

| | | | |
|---|---|---|---|
| 4,838,862 A | 6/1989 | Baker et al. | |
| 5,368,571 A | 11/1994 | Horres, Jr. | |
| 5,571,261 A * | 11/1996 | Sancoff ............. | A61M 5/14593 222/399 |
| 5,578,005 A | 11/1996 | Sancoff et al. | |

FOREIGN PATENT DOCUMENTS

WO WO-02087976 A2 * 11/2002 ............. B65D 83/62

OTHER PUBLICATIONS

International Search Report and Written Opinion for Application No. PCT/US2023/029992, dated Dec. 21, 2023, 21 pages.
Invitation to Pay Additional Fees, and Where Applicable, Protest Fee and Partial International Search Report for Application No. PCT/US2023/029992, dated Oct. 30, 2023, 15 pages.
Banister, et al., "Molecular Engineering of Polymer Actuators for Biomedical and Industrial Use", Proc. SPIE 8340, Electroactive Polymer Actuators and Devices (EAPAD) 2012, 83400D (Apr. 3, 2012); https://doi.org/10.1117/12.917495.
Banister, et al., "Study of a Smart Polymer Medical Device, Product Development Obstacles and Innovative Solutions", Proc. SPIE 8343, Industrial and Commercial Applications of Smart Structures Technologies 2012, 83430I (Mar. 29, 2012); https://doi.org/10.1117/12.915529.

* cited by examiner

*Primary Examiner* — Laura A Bouchelle
(74) *Attorney, Agent, or Firm* — MASCHOFF BRENNAN

(57) ABSTRACT

Activatable medicament delivery containers and assemblies are disclosed that can be activated to direct a medicament from the container using an expandable material that causes an expansion chamber to displace the medicament from the container, where the medicament can be directed from the container at a predetermined or use-specific rate, and for a predetermined period of time, and the container being couplable with a dock to form an activatable medicament delivery assembly, where the container can be removably coupled or replace with the dock, and where the dock can be coupled directly to an intravenous fluid delivery device.

17 Claims, 11 Drawing Sheets

ACTIVATABLE MEDICAMENT DELIVERY CONTAINERS AND ASSEMBLIES

BACKGROUND

The present disclosure relates generally to the movement of medical fluid such as an intravenous (IV) fluid, and more particularly, to activatable medicament delivery containers and assemblies.

Fluids used for medical treatment, which are also known as medicaments, can be directed to a patient from a container, such as an IV bag. IV bags can be made from materials that include plastic forming an inner cavity configured to contain a fluid or medicament under vacuum. The IV bag is fluidly coupled with tubing that connects the IV bag to delivery device, such as a catheter or a needle in the patient's vein.

IV bags rely on gravity to direct a fluid out of the bag or a mechanical infusion pump that draws the fluid out of the bag. In accordance with at least some embodiments disclosed herein is the realization that infusing intravenous fluids by gravity or using an infusion pump requires skilled operation, can have operation characteristics that are affected by numerous factors, can increase the potential for contamination of the fluid and/or infection of a patient, and can limit the mobility of the patient.

The factors which can affect operation of medicament containers that rely upon gravity can include, but are not limited to, requiring a ventilation passage to resist creation of a vacuum in the container as fluid moves out of the container, or requiring the container to be collapsible to resist creation of a vacuum in the container. Additionally, a flow rate of the fluid moving out of the container is often controlled downstream from the container using an orifice along the fluid pathway. Further, fluid flow characteristics can be affected by external or ambient pressure, as well as orientation, position, and a head height of the container relative to the patient.

Medicament containers that are configured for use with an infusion pump rely upon a skilled operator to couple the container and tubing with the infusion pump, and to set the desired flow rate. Additionally, a patient receiving infusion therapy with an infusion pump must transport the infusion pump with them if they are to continue receiving the infusion therapy, thereby limiting mobility of the patient, such as during transportation to or within a medical care facility. Further, if the medicament container and corresponding tubing are separated from the patient, the potential for contamination of the fluid and/or infection of the patient is increased. Furthermore, the absence of a fluid moving through a patient's catheter can increase the likelihood of catheter occlusion.

As such, medicament containers that rely on gravity or an infusion pump can be susceptible to flow rate drift which can result in under or over infusion of a medicament to the patient, can increase the potential for contamination of the fluid and/or infection of the patient, and can limit mobility of the patient.

SUMMARY

Aspects of the present disclosure provide medicament containers that can be activated to direct a fluid out of the container a desired flow rate without relying on complex procedures for preparation and configuration of the container, a head height of the container, internal resistance to regulate fluid flow rate, or gravity or an infusion pump to move the fluid. The present disclosure also provides activatable medicament delivery containers and assemblies that can be fluidly coupled with infusion devices, such as a catheter or syringe, to maintain patency and reduce the likelihood of occlusion to the infusion device.

Some instances of the present disclosure provide an activatable medicament delivery container comprising a body comprising an inner surface defining a medicament chamber, an expansion chamber, and an activation chamber, a medicament port forming a passage fluidly coupled with the medicament chamber, a pressure membrane that fluidly separates medicament chamber and the expansion chamber and a breakable membrane comprising a first configuration wherein the breakable membrane fluidly separates the expansion chamber and the activation chamber, and a second configuration wherein the breakable membrane forms a passage between the expansion chamber and the activation chamber, wherein, when the breakable membrane is in the second configuration, an activator material within the activation chamber can contact an expandable material within the expansion chamber through the passage, such that a volume of the expansion chamber increases, thereby displacing a pressure membrane toward the medicament chamber to increase a pressure therein.

In some instances, the present disclosure provides a method of delivering a medicament from an activatable medicament delivery container, the method comprising causing a breakable membrane, which fluidly separates an expansion chamber from an activation chamber, to break such a passage is formed between the expansion chamber and the activation chamber, and an activator material within the activation chamber contacts an expandable material within the expansion chamber through the passage, wherein, contact between the activator material and the expandable material cause a volume of the expansion chamber to increase such that a pressure membrane fluidly separating a medicament chamber from the expansion chamber is displaced toward the medicament chamber, thereby increasing a pressure within the medicament chamber and directing a medicament out of the medicament chamber through a medicament port.

The present disclosure also provides, in some instances, an activatable medicament delivery container comprising a body comprising an inner surface defining a first chamber, a second chamber, and a third chamber, a medicament port forming a passage fluidly coupled with the first chamber, and a breakable membrane comprising a first configuration wherein the breakable membrane fluidly separates the second chamber and third chambers, and a second configuration wherein the breakable membrane forms a passage between the second chamber and third chambers, wherein, when the breakable membrane is in the second configuration, an activator material within the third chamber can contact an expandable material within the second chamber through the passage, such that a volume of the second chamber increases, thereby displacing a pressure membrane toward the first chamber to increase a pressure within the first chamber.

In some instances of the present disclosure, an activatable medicament delivery assembly is provided comprising an activatable medicament delivery container comprising an inner surface defining a medicament chamber, an expansion chamber, and a medicament port forming a passage fluidly coupled with the medicament chamber, and a dock comprising a fluid connector, wherein, when the container is coupled with the dock, the medicament port is fluidly coupled with a first inlet port of the fluid connector, wherein, the container is activatable such that an expandable material within the expansion chamber increases a volume of the expansion chamber, thereby displacing a pressure membrane toward the medicament chamber to increase a pressure in the medicament chamber and direct a medicament out of the medicament port and through the fluid connector.

In some instances, the present disclosure provides a method of delivering a medicament from an medicament delivery assembly, the method comprising coupling an activatable medicament delivery container to a dock so that a medicament port of the container is fluidly coupled with a first inlet port of a fluid connector of the dock, and activating the container such that an expandable material within an expansion chamber of the container increases a volume of the expansion chamber, thereby displacing a pressure membrane, fluidly separating the expansion chamber from a medicament chamber of the container, toward the medicament chamber to increase a pressure in the medicament chamber and direct a medicament out of the medicament port and through the fluid connector.

Accordingly, the present application addresses several operational challenges encountered in prior medicament delivery containers and assemblies and provides numerous improvements that reduce complexity related to preparation and delivery of fluids to a patient, reduce the likelihood of occlusion and infection, and enable greater patient mobility.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1:
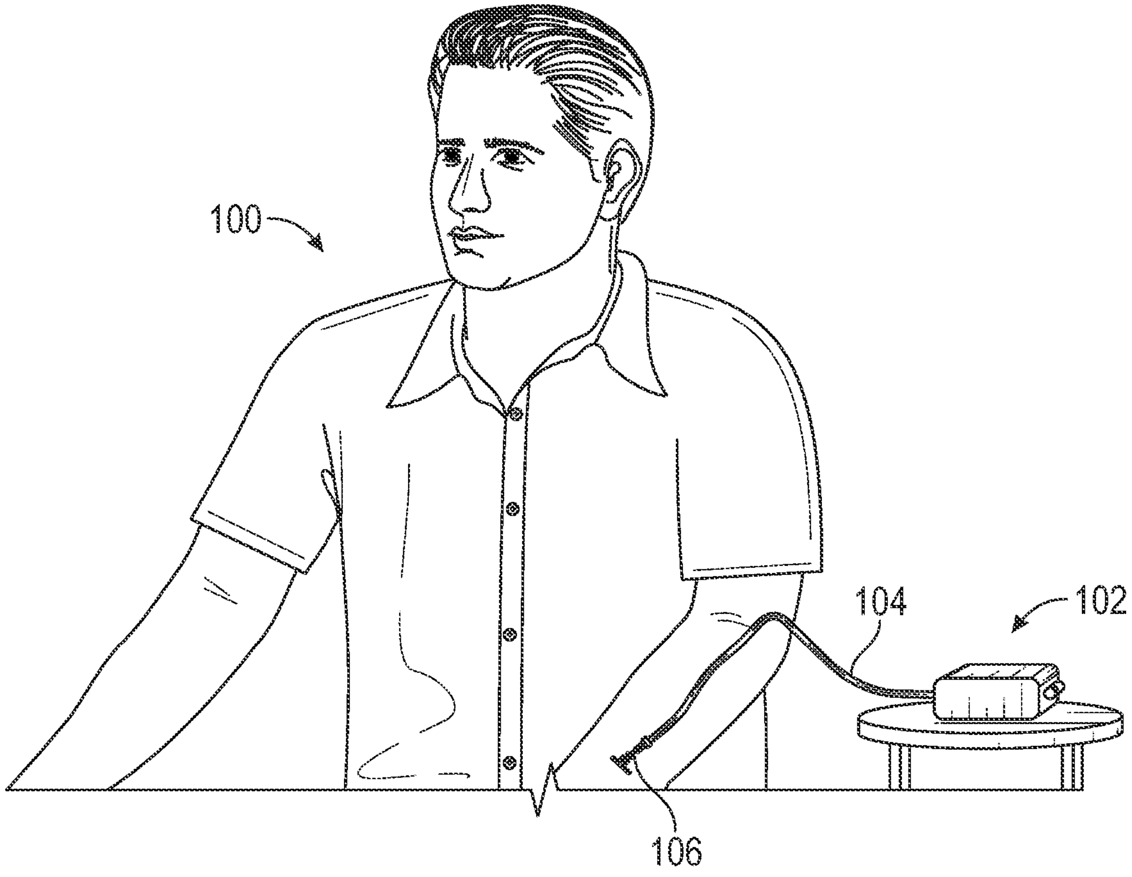
FIG. 1 illustrates an activatable medicament delivery container coupled to a patient through IV tubing, in accordance with aspects of the present disclosure.
Figure 2:
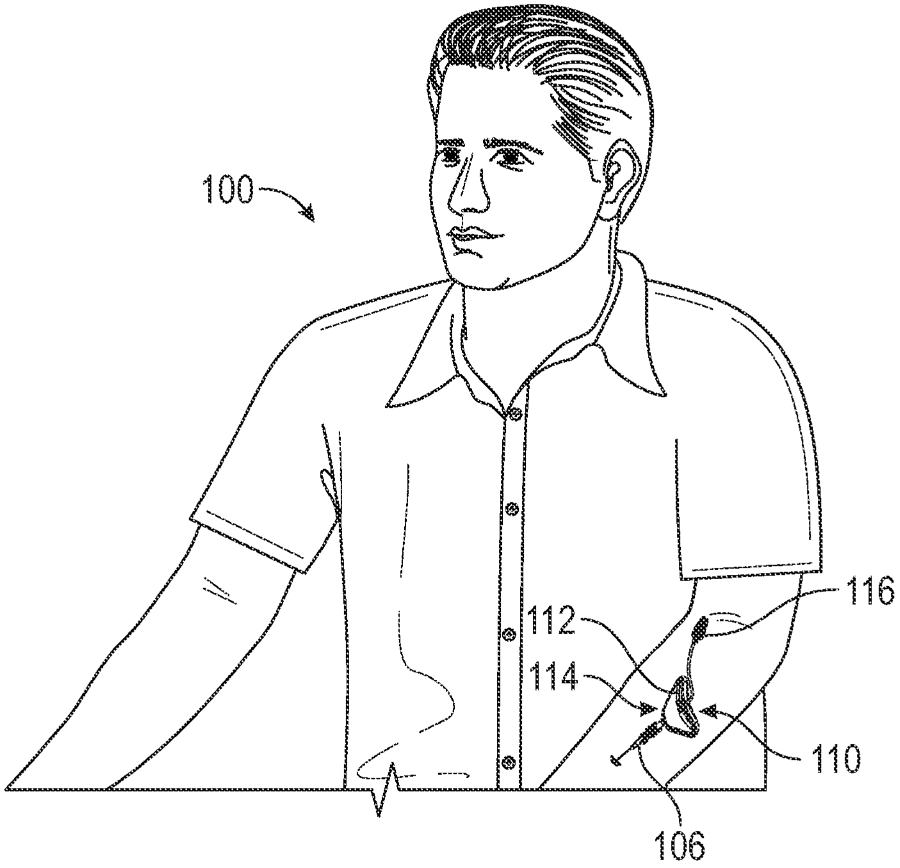
FIG. 2 illustrates another activatable medicament delivery container and an activatable medicament delivery assembly coupled to a patient through a catheter, in accordance with aspects of the present disclosure.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, any embodiment of the present disclosure can be used in other fluid conveyance systems. Furthermore, various applications of such embodiments and modifications thereto, which may occur to those who are skilled in the art, are also encompassed by the general concepts described herein.

In accordance with some embodiments, the present application discloses various features and advantages of activatable medicament delivery containers and assemblies. The present disclosure can provide for more efficient, safer, and more reliable delivery of medicament by providing activatable medicament delivery containers and assemblies, which can be used in a variety of settings and circumstances, can eject a medicament at a constant, user-selected, rate.

Activatable medicament delivery containers and assemblies having features of the present disclosure can be used in settings and circumstances in which the patient mobility or ambient atmospheric conditions may interfere with conventional medicament delivery methods, such as in an emergency medical treatment situation outside of a care facility, during flight, below sea level, where there is no electricity to power an intravenous pump, or when a patient is being transported.

Activatable medicament delivery containers and assemblies having features of the present disclosure can be configured to eject a medicament at a constant rate upon activation of the container. Additionally, in accordance with some embodiments, various features and advantages of the present application can eject a medicament at a user-selected rate when the container is activated. In some aspects, activatable medicament delivery containers of the present disclosure are removable and replaceable to permit continuous delivery of a medicament to a patient, change a type of medicament being delivered, or to provide delivery of a medicament at a later time.

Activatable medicament delivery containers of the present disclosure can include one or more chamber configured to retain any of a substance, such as a medicament, an expanding material, and an activator material, therein. In some aspects of the present disclosure, one or more chamber can be formed by separate portions of a medicament container or separate medicament containers, wherein the separate portions or separate medicament containers can be assembled together.

In at least some embodiments of the present disclosure, an activatable medicament delivery container can include a medicament chamber and an expansion chamber, wherein, when the container is activated, an expandable material within the expansion chamber causes a volume of the expansion chamber to increase and thereby displace a medicament from the medicament chamber.

Some embodiments of the present disclosure provide that an activatable medicament delivery container can include an activation chamber having an activator material therein, wherein the container is activated by causing the activator material to contact the expandable material in the expansion chamber. The container can be activated by any suitable means, such as by breaking, squeezing, or biasing the activation chamber. In some aspects of the present disclosure, a passage between the expansion chamber and the activation chamber is formed when the container is activated.

In some embodiments of the present disclosure, an activatable medicament delivery container is activated, such that the expandable material causes a volume of the expansion chamber to increase, when an electrical current is applied to any of the container, the expandable material, and the activator material. The container can be activated when an electrical circuit between the container and a power source is completed, such as when the container is connected to a dock, moving a switch, removing a tab, or by sending a signal.

When the activatable medicament delivery container is activated, a volume of the expansion chamber increases so that at least a portion of the medicament chamber is displaced, thereby increasing a pressure within the medicament chamber such that a medicament is directed or ejected out of the medicament chamber through a medicament port of the container.

In at least some embodiments of the present disclosure, an activatable medicament delivery container assembly can include an activatable medicament delivery container and a dock configured to couple with the container.

The dock can include one or more fluid passage to receive a fluid from an activatable medicament delivery container and directed the fluid out of the dock. The dock can include a fluid passage having more than one fluid inlet such that a fluid from the container and another source can be directed through the dock. In some aspects of the present disclosure, the dock can be configured to activate the container. In some embodiments of the present disclosure, the dock can form a portion of or couple with a fluid delivery device, such as a peripheral intravenous catheter or a syringe.

Referring now to the figures, FIG. 1 illustrates a patient 100 coupled to an activatable medicament delivery container 102 through intravenous tubing 104 and a peripheral intravenous catheter 106. Because the container 102 is not dependent on the position of the container relative to another fluid source or an intravenous pump, the patient can move with the container 102. For example, a patient can begin to receive a medicament from the container 102 at the scene of an emergency or accident, and the patient can continue to receive medicament from the container 102 while being loaded into and out of an ambulance, during transportation to a care facility, and within the care facility, without the needing to maintain a position of the medicament container above the patient or connecting the medicament container to an intravenous pump.

The activatable medicament delivery container 102 can be configured to include a user-selectable flow rate so that the flow rate of medicament ejected from the container can be selected when the container is activated. Additionally, in some embodiments, the flow rate of medicament ejected from the container can be increased after activation.

In some embodiments of the present disclosure, an activatable medicament delivery assembly 110 can be coupled to a patient 100 through a peripheral intravenous catheter 106, where the activatable medicament delivery assembly 110 includes an activatable medicament delivery container 112 and a dock 114. The activatable medicament delivery assembly 110 is configured to direct a first medicament from the 112 to the patient 1, and can include a fluid passage configured to receive and direct a second medicament to the patient. For example, the activatable medicament delivery assembly 110 can include an IV set 116 so that a second medicament can be injected into the patient, as needed, while the first medicament is continuously directed to the patient from the activatable medicament delivery container 112.

Figure 3:
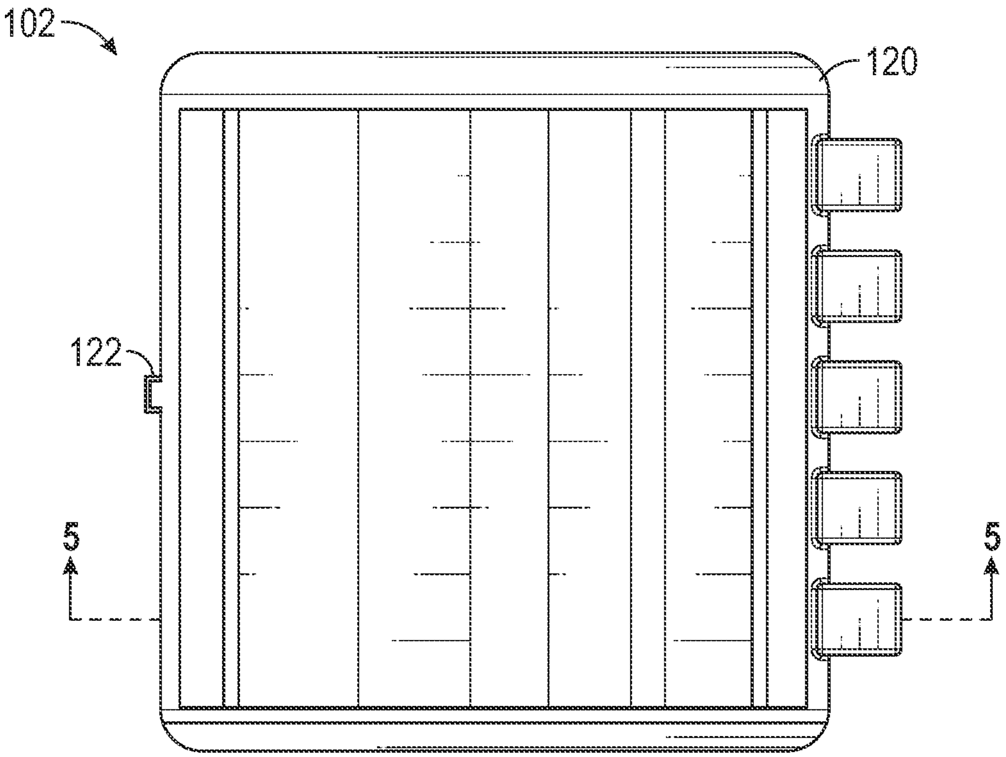
FIG. 3 illustrates a top view of an activatable medicament delivery container, in accordance with aspects of the present disclosure.
Figure 4:
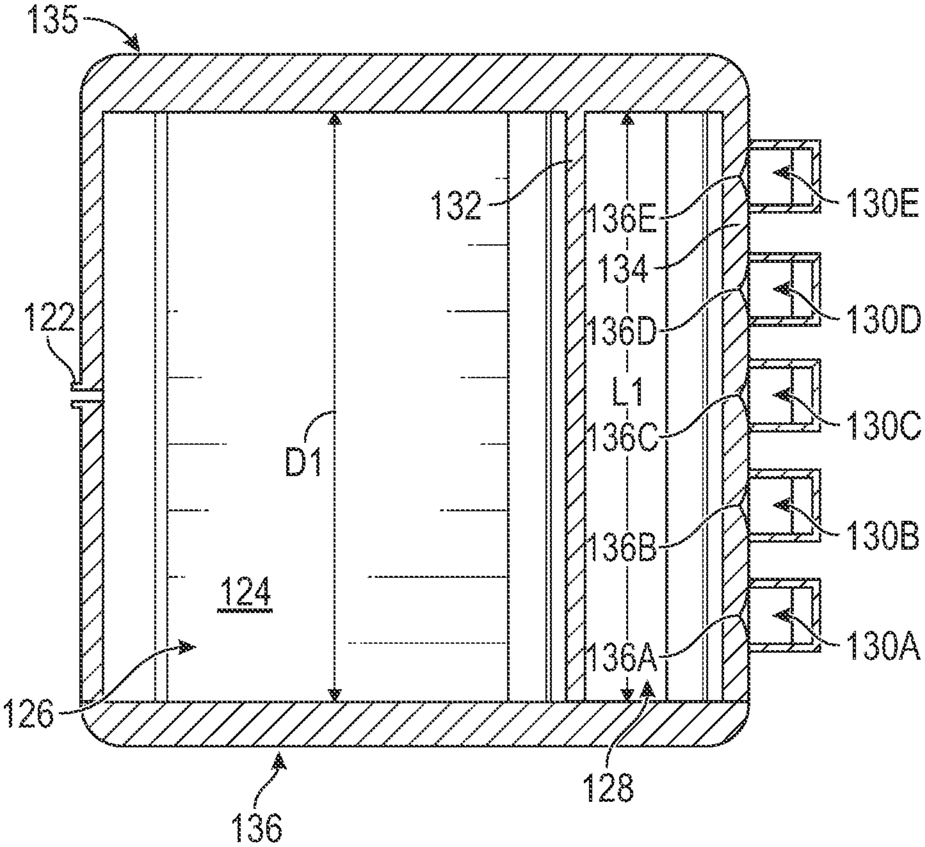
FIG. 4 illustrates a cross-sectional top view of the activatable medicament delivery container of FIG. 3, in accordance with aspects of the present disclosure.

FIG. 3 illustrates an activatable medicament delivery container 102 having a body 120 with a medicament port 122 and an inner surface forming a plurality of chambers. The inner surface 124 and the chambers of the body are shown in the cross-sectional top view of FIG. 4. The inner surface 124 forms a medicament chamber 126, an expansion chamber 128, and activation chambers 130A-130E. Although more than one activation chamber is shown, it should be understood that the present disclosure contemplates embodiments in which the container 102 has one activation chamber.

Each of the medicament chamber 126, the expansion chamber 128, and the activation chambers 130A-130E are fluidly separated from each other. The medicament chamber 126 is fluidly separated from the expansion chamber 128 by a pressure membrane 132, and the expansion chamber 128 is fluidly separated from the activation chambers 130A-130E by a breakable membrane 134.

The breakable membrane 134 can include a portion that is configured to break or tear to form a passage between the expansion chamber 128 and an activation chamber 130A-130E. In some embodiments, the breakable membrane 134 includes a channel 136A-136E that extends partially into the breakable membrane 134. The channel 136A-136E can extend into the breakable membrane 134 in direction from the expansion chamber 128 toward an activation chamber 130A-130E, or from an activation chamber 130A-130E toward the expansion chamber 128. In embodiments in which the container 102 includes more than one activation chamber 130A-130E, each activation chamber 130A-130E can be aligned with a respective channel 136A-136E.

It should be understood that the present disclosure contemplates embodiments in which the container includes one activation chamber. Additionally, it is contemplated that the container can have a first activation chamber and a second activation chamber, wherein the first activation chamber comprises a first volume, and the second activation chamber comprises a second volume that is a different volume than the first volume.

In some embodiments of the present disclosure, the container 102 can include other means of forming a passage between the expansion chamber 128 and an activation chamber 130A-130E when the container 102 is activated. For example, the container 102 can include a piercing member or needle that is configured to puncture the breakable membrane 134 and form a fluid passage between the expansion chamber 128 and an activation chamber 130A-130E. In some aspects of the present disclosure, a fluid passage between the expansion chamber 128 and an activation chamber 130A-130E can include a valve that is configured to open the fluid passage when container 102 is activated.

When the container 102 is activated, an activator material is directed through a fluid passage, from the activation chamber 130A-130E to the expansion chamber 128, so that the activator material contacts an expandable material within the expansion chamber 128. The expandable material is configured to increase a volume and/or pressure within the expansion chamber 128, thereby moving the pressure membrane 132 away from the expansion chamber 128 and toward the medicament chamber 126.

The pressure membrane 132, or at least a portion thereof, extends between the medicament chamber 126 and the expansion chamber 128 to form a fluid separation therebetween. The pressure membrane 132 has a first length L1 that extends between a first side 135 and a second side 136 of the container 102, and a second length L2 that extends in a direction that is transverse, relative to the length L1. The first length L1 can be greater that a distance D1 between the first and second sides 135, 136 of the container, and/or the second length L2 can be greater that a distance D2 between the top side 138 and the bottom 140 of the container.

The length L1, L2 of the pressure membrane 132 is configured to permit at least a portion of the pressure membrane 132 to move in a direction from the expansion chamber 128 toward the medicament chamber 126 when the container 102 is activated. When then the pressure membrane 132 moves toward the medicament chamber 126, a volume of the medicament chamber 126 decreases and a pressure within the medicament chamber 126 increases such that a medicament is directed out of the medicament chamber 126 through the medicament port 122.

The medicament chamber 126 and the expansion chamber 128 can each have a specific volume configured to direct a desired amount of the medicament out of the medicament chamber 126 when the expansion chamber 128 is fully expanded. In some embodiments of the present disclosure, the expansion chamber 128 has a volume configured to completely displace the medicament in the medicament chamber 126 when the expansion chamber 128 is fully expanded. Additionally, an expansion characteristic of the expandable material can be selected to achieve a desired displacement of the medicament from the medicament chamber 126. In some aspects of the present disclosure, the expandable material has a three-to-one expansion ratio, and the expansion chamber 128 is one-third of the volume of the medicament chamber 126.

Figure 5A:
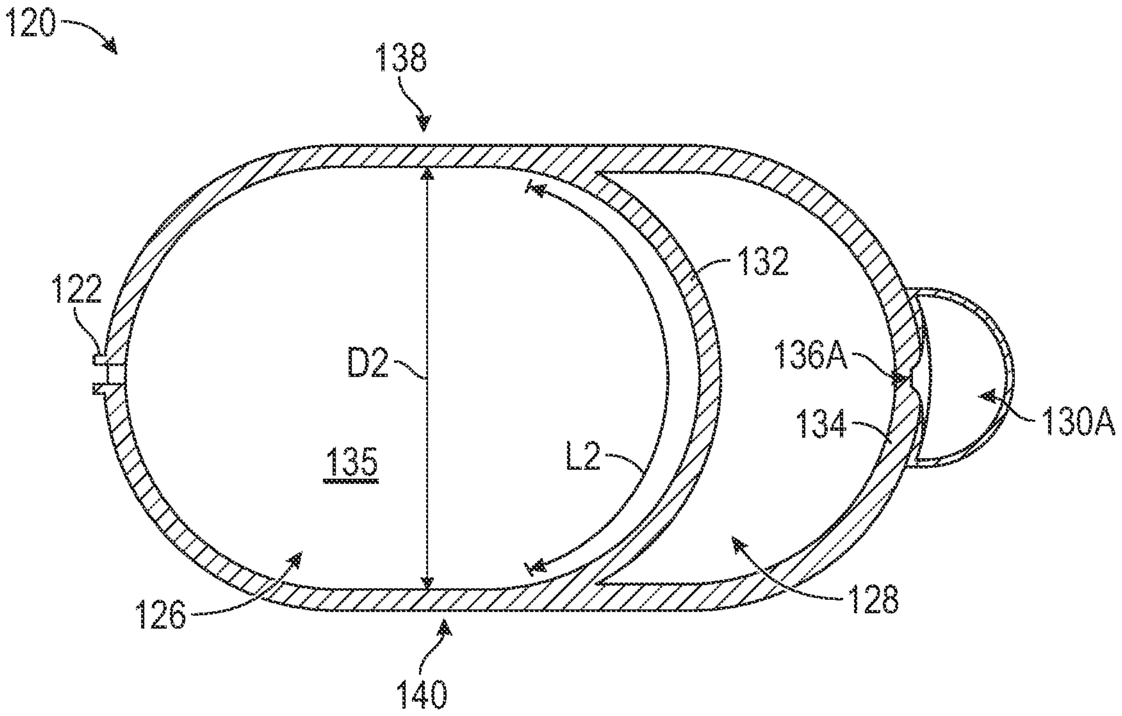
FIGS. 5A-5D illustrate cross-sectional side views of the activatable medicament delivery container of FIG. 3, in accordance with aspects of the present disclosure.

To direct the medicament out of the medicament chamber 126, the expansion chamber 128 can have a volume that is configured to approximately displace all the medicament completely Activation of an embodiment of the container 102 is illustrated in FIGS. 5A-5D, which show a cross-sectional side view along the line 5-5 of FIG. 3. The position of the pressure membrane 132, relative to the medicament chamber 126 and the expansion chamber 128 before activation of the container 102, is shown in FIG. 5A. The pressure membrane 132 has a length L2 that extends between the top and bottom 138, 140 of the container. The length L2 of the pressure membrane 132 is greater than a distance D2 between the top and bottom 138, 140 of the container. As such, at least a portion of the pressure membrane 132 extends toward the expansion chamber 128 when the container 102 is not activated. However, it is also contemplated that a portion of the pressure membrane 132 can extend toward the medicament chamber 126 when the container 102 is not activated.

In some embodiments of the present disclosure, the pressure membrane 132 comprises a flexible material, relative to a material of the body 120, such that at least a portion of the pressure membrane 132 can bias or stretch toward the medicament chamber 126 when the container 102 is activated. Thus, the pressure membrane 132 can have a length L2 that is approximately equal to, greater than, or less than the distance D2 between the top and bottom 138, 140 of the container.

Figure 5B:
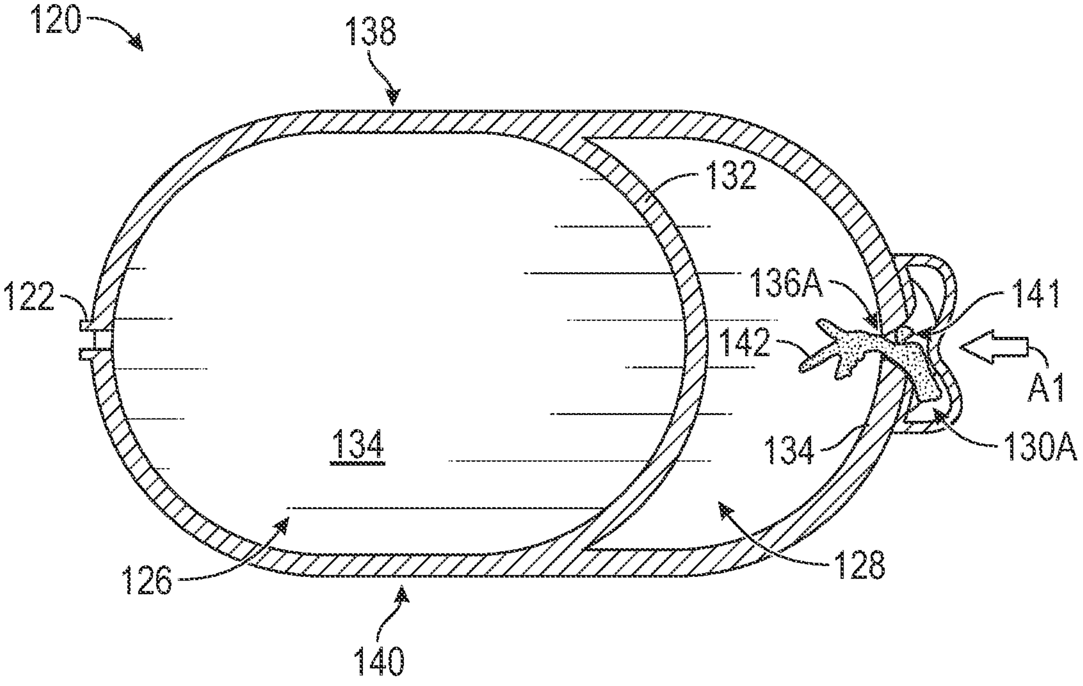

The container 102 can be activated by any of squeezing, compressing, and/or biasing the activation chamber, as shown in FIG. 5B. When the activation chamber 130A is compressed, as illustrated by arrow A1, a fluid passage 141 is formed through the breakable membrane, from the activation chamber 130A to the expansion chamber 128. A activator material 142 can move from the activation chamber 130A to the expansion chamber 128, wherein the activator material 142 can contact an expandable material in the expansion chamber 128.

In some embodiments, a first activation chamber 130A comprises a first volume of activator material, and a second activation chamber 130B comprises a second volume of activator material.

In embodiments where the first and second volume of activator material is approximately equal, the container 102 can be activated by compressing the first activation chamber 130A so that the medicament is ejected from the container 102 at a first rate. If the second activation chamber 130B is compressed, the medicament can be ejected from the container 102 at a second rate, which is approximately twice the first rate. For example, each of the activation chambers 130A-130E can contain a volume of activator material configured to eject the medicament at a rate of approximately 5 milliliters per second. If two activation chambers are compressed, the medicament can be ejected from the container 102 at a rate of approximately 10 milliliters per second.

In embodiments where the first and second volume of activator material are different, the container 102 can be activated by compressing the first activation chamber 130A so that the medicament is ejected from the container 102 at a first rate. If the second activation chamber 130B is compressed, the medicament can be ejected from the container 102 at a second rate, which is the sum of the first and second rates. For example, the medicament can be ejected from the container 102 at a rate of approximately 8 milliliters per second by compressing a first activation chamber 130A configured to eject the medicament at a rate of approximately 3 milliliters per second, and a second activation chamber 130B configured to eject the medicament at a rate of approximately 5 milliliters per second.

It should be understood that the activator material can be any material configured to cause the expandable material to increase in volume within the expansion chamber 128. For example, the activator material can be water or any gaseous, solid, liquid, or amorphous material configured react with the expandable material. The expandable material can also be any material configured to react with the activator material so that a pressure within the expansion chamber increases. In some embodiments of the present disclosure, the expandable material comprises an expandable polymer. For example, the expandable material can be an expandable polymer that increases in volume at a rate that is proportional to the volume of activator material that contacts the expandable material.

Figure 5C:
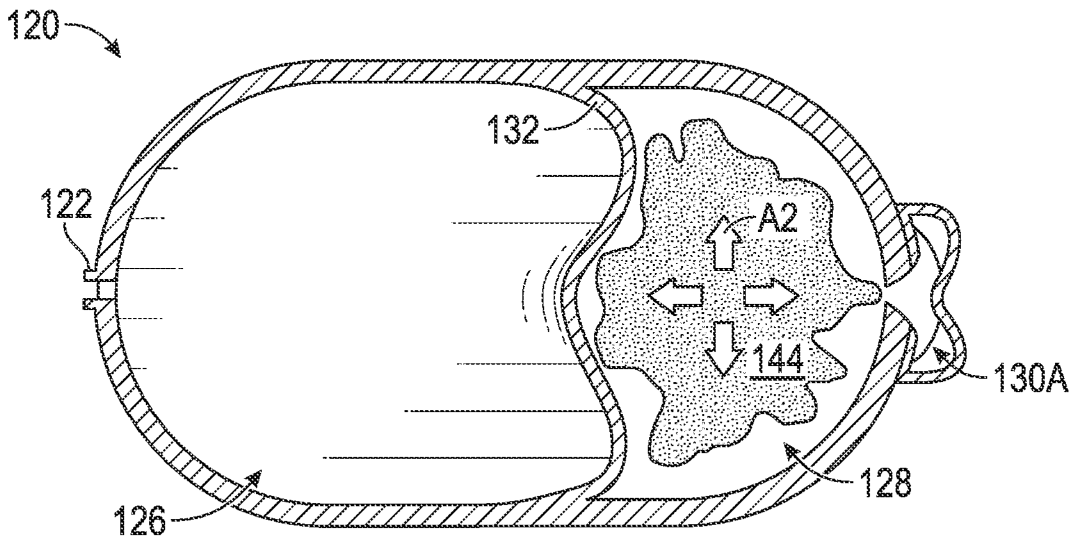

Contact between the activator material 142 and the expandable material 144 causes the volume of the expansion chamber 128 to increase, as illustrated in FIG. 5C. As the expandable material 144 expands to increase the volume of the expansion chamber 128, as shown by arrow A2, a portion of the pressure membrane 132 is displaced toward the medicament chamber 126, thereby decreasing a volume and increasing a pressure within the medicament chamber 126.

Figure 5D:
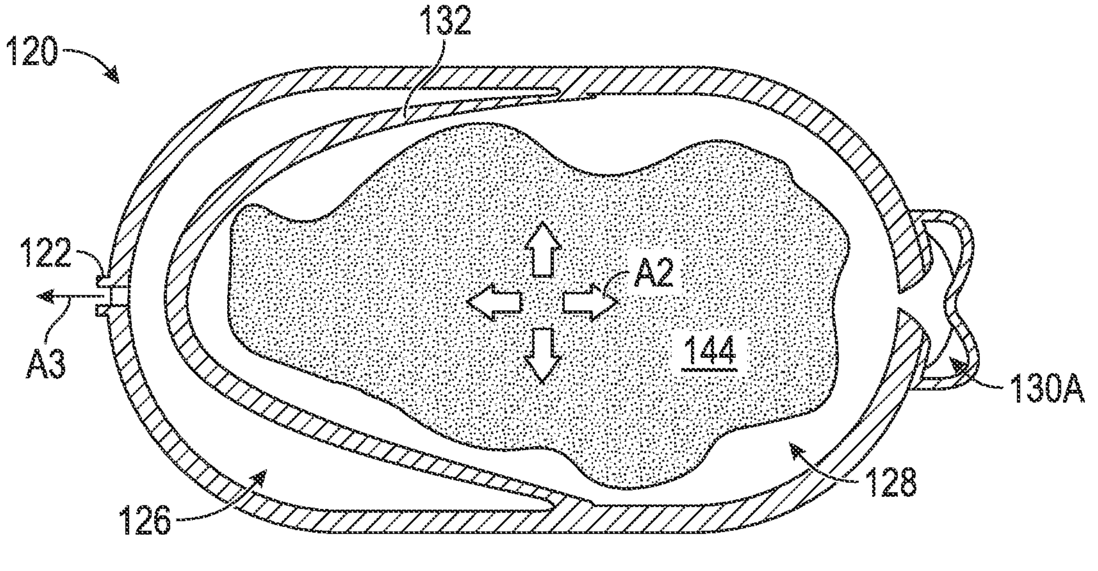
Figure 6:
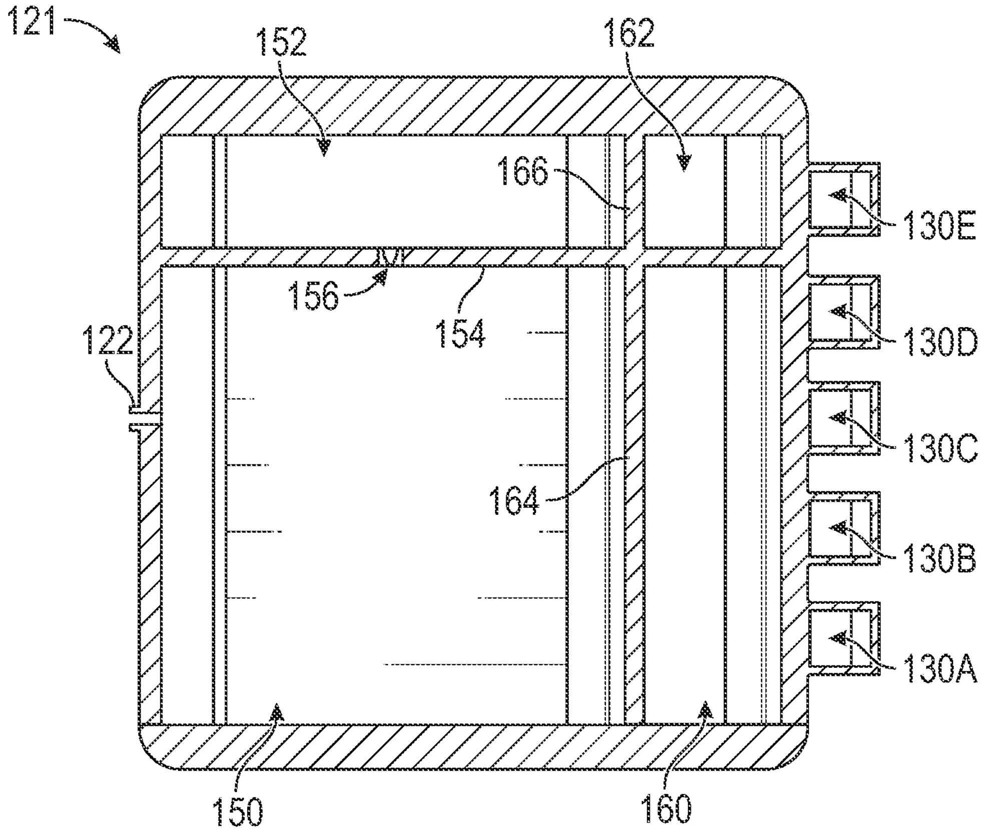
FIG. 6 illustrates a top perspective view of another activatable medicament delivery container, in accordance with aspects of the present disclosure.

The expandable material 144 can continue to causes the volume of the expansion chamber 128 to increase, thereby moving the pressure membrane 132 further toward the medicament chamber 126, as illustrated in FIG. 5D.

As the pressure membrane 132 is displaced toward the medicament chamber 126, a medicament is ejected from the medicament chamber 126 through the medicament port 122, as illustrated by arrow A3.

In some embodiments, the medicament port 122 can be configured to fluidly couple with IV tubing or another device. In some aspects of the present disclosure, the medicament port 122 can include any of a luer connector or threads configured to connect with another device, such as an IV set, catheter, or syringe.

In some embodiments of the present disclosure, an activatable medicament delivery container 121 can be configured to contain more than one medicament that can be separately activated, so that the container 102 can be activated to eject a first medicament, and can be activated again to ejected a second medicament. The second medicament can be ejected at the same time or after the first medicament is ejected from the container. In some aspects of the present disclosure, the second medicament can be ejected into the medicament container for the first medicament or directly to a medicament port for the first medicament, or to a second medicament port.

To contain more than one medicament, the container 121 can include a first medicament chamber 150 and a second medicament chamber 152 that are fluidly separated by a medicament membrane 154. The container 121 can include a fluid passage 156 between the first and second medicament chambers, such that a second medicament can move from the second medicament chamber 152 to the first medicament chamber 150. The fluid passage 156 between the first and second medicament chambers can be formed by any means configured to direct the second medicament from the second medicament chamber 152 to the first medicament chamber 150, such as a breakable portion or a valve.

The container 1121 can also include a first expansion chamber 160 and a second expansion chamber 162, positioned adjacent to the first medicament chamber 150 and the second medicament chamber 152, respectively. When a first activation chamber 130A-130D is compressed to activate the container 121, a first pressure membrane 164 can be displaced to eject the first medicament from the first medicament chamber 150. If another activation chamber 130E, adjacent the second expansion chamber 162, is activated, a second pressure membrane 166 can be displaced to eject the second medicament from the second medicament chamber 152.

Figure 7:
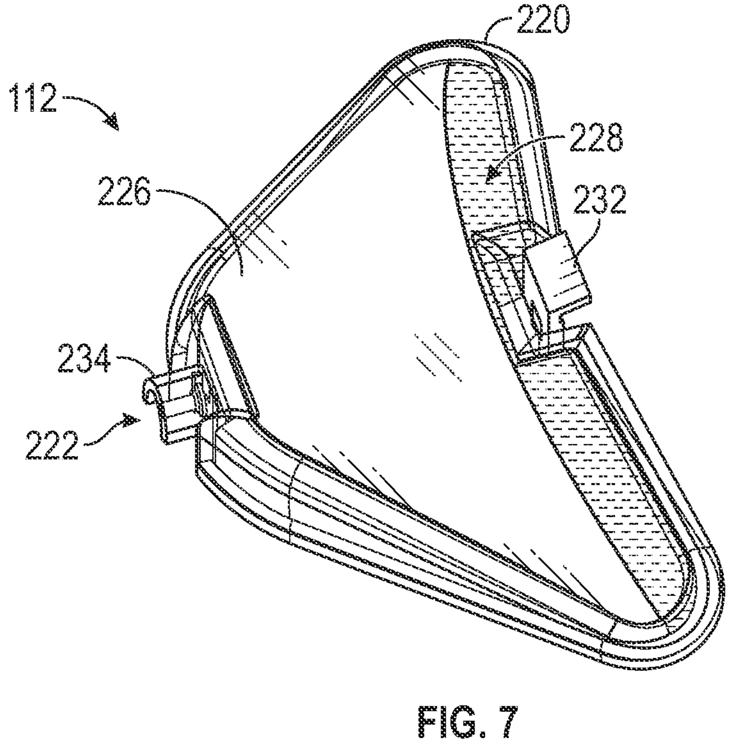
FIG. 7 illustrates a top perspective view of another activatable medicament delivery container, in accordance with aspects of the present disclosure.

Referring now to FIG. 7, the present disclosure also contemplates embodiments of an activatable medicament delivery container 112 having a body 220 with a medicament port 222 and an inner surface forming a medicament chamber 226 and an expansion chamber 228.

In some embodiments of the present disclosure, the container 112 can have a tab 232 that can engage against a dock to resist separation of the container 112 from the dock. The container 112 can also have a protrusion 234 that can be received into a channel of the dock to also resist separation of the container 112 from the dock. In some aspects of the present disclosure, any of the container 112 or the dock can include a tab, protrusion, or sleeve that is configured to engage with the other of the container 112 or the dock.

The container 112 can be activated to eject a medicament from the medicament chamber 226 by directing an electrical current to the expandable material. To direct an electrical current to the expandable material, the container 112 can include a battery or power input port. The container 112 can be configured to be activated so that an electrical current is directed to the expandable material using means for completing an electrical current and/or sending a signal to direct an electrical current to the expandable material, including, but not limited to, a switch, a knob, and a removable tab.

Figure 8:
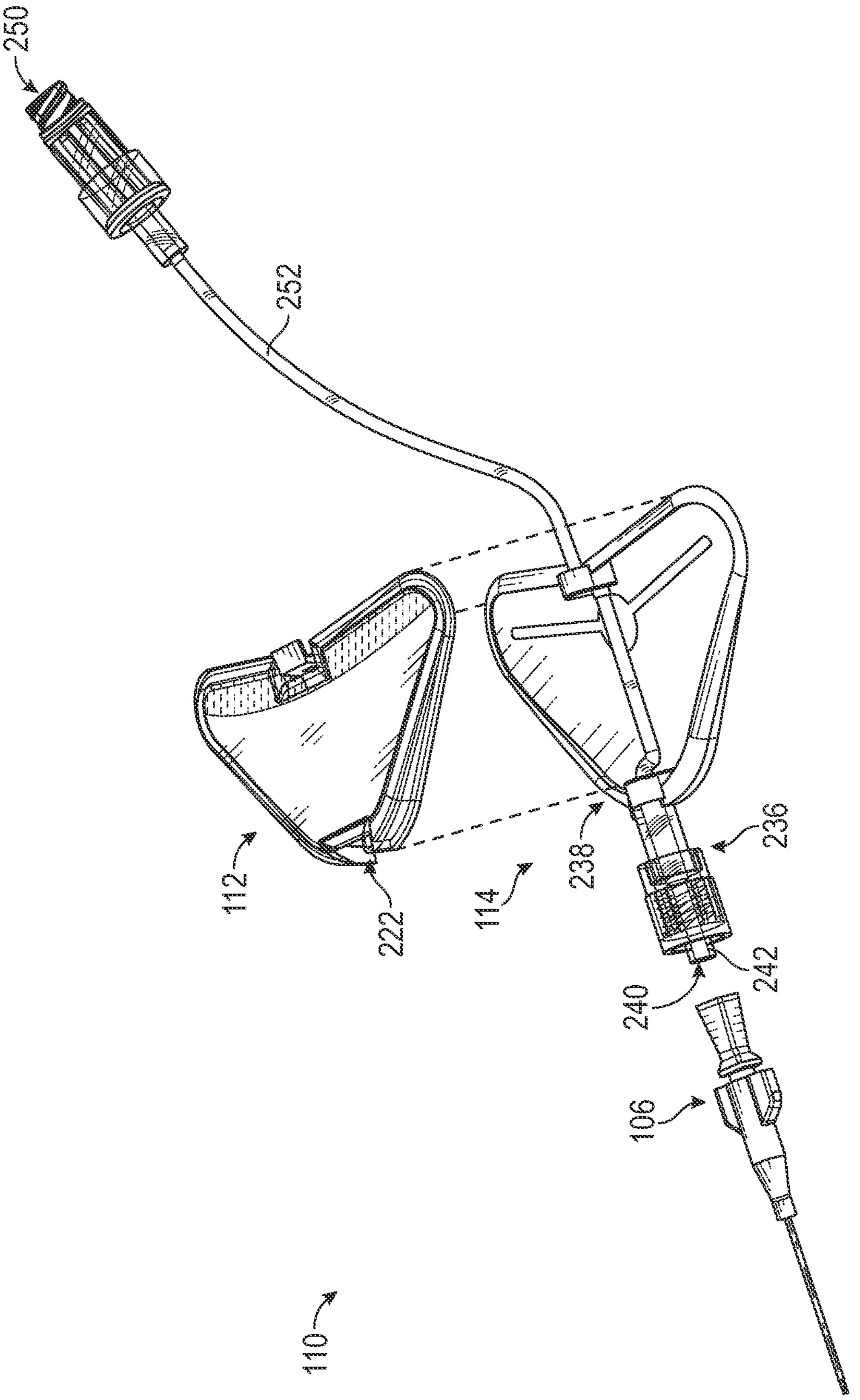
FIG. 8 an exploded top perspective view of an activatable medicament delivery assembly, including the activatable medicament delivery container of FIG. 7, in accordance with aspects of the present disclosure.

Any of the containers 102, 112, 121 of the present disclosure can couple with a dock 114 to form an activatable medicament delivery container assembly 110 as illustrated in FIG. 8. The dock 114 is configured to couple with a container 102, 112, 121, receive a fluid from the container 102, 112, 121, and directed the fluid from the container 102, 112, 121.

The dock 114 can be configured to couple with a medicament delivery device, such as a peripheral intravenous catheter or a syringe. In some embodiments of the present disclosure, the dock 114 can form a portion of a medicament delivery device, such as, for example, a device configured to secure a catheter to a patient.

In use, a caregiver can couple the dock 114 to a fluid delivery device, such as a catheter 106 inserted into a patent's vein. If the dock includes an adhesive, such as when the dock 114 is configured to secure the catheter to the patient, the dock 114 can be adhered to the patient. Next, an activatable medicament delivery container 102, 112, 121 can be coupled with the dock 114 and the container can be activated to direct a medicament from the container and into the fluid delivery device.

Embodiments of the present disclosure can be used to direct any kind of medicament to the fluid delivery device, including medication or saline to prevent occlusion of the catheter or a needle. Further, a caregiver can inject an additional medicament into the patient by directing the fluid through a second input flow port.

The activatable medicament delivery container assembly 110 can be configured so that the container 102, 112, 121 is activated upon coupling the container with the dock, or the container 102, 112, 121 can be activated after coupling the container with the dock.

In any of the embodiments of the present disclosure, the body 120, 220 or any portion of the container 102, 112, 121 can include a material that is transparent to permit visualization observation to within the body. The transparent material can form a window to permit observation of any of the medicament chamber, the medicament, the expansion chamber, the expansion material, the activation chamber, and the activator material.

The activatable medicament delivery container assembly 110 can also be configured so that the container 102, 112, 121 is removably coupled with the dock 114, which could permit the container 102, 112 to be replaced with a second container if the medicament in the first container is empty or to change to a different medicament that the medicament in the first container.

FIG. 8 illustrates an activatable medicament delivery container assembly 110, which includes a container 112 and a dock 114.

The dock 114 includes a fluid connector 236 having a first inlet port 238, an outlet port 240, and a fluid passage that extends from the first inlet port 238 to the outlet port 240. The first inlet port 238 can fluidly couple with a medicament port 222 of the container 112 when the container is coupled with the dock.

When the container 112 is activated, the medicament can be ejected from the container 112 into the first inlet port 238 and can move through the fluid passage to the outlet port 240 of the fluid connector 236.

The fluid connector 236 of the dock can be configured to couple with tubing or another device. The fluid connector 236 can have threads, other connection means, or be configured to form an interference fit with tubing or another device. In some aspects of the present disclosure, the fluid connector 236 comprises a luer connector 242 that can be coupled with another medicament delivery device. The medicament delivery device can include any of a peripheral intravenous catheter 106 or a syringe. In some aspects of the present disclosure, a portion of the dock forms a medicament delivery device, e.g., a catheter or a syringe, to form a unitary structure.

In some embodiments of the present disclosure, the dock 114 includes a second inlet port 250 and second fluid passage 252 configured direct a fluid through the dock. The second fluid passage 252 be coupled to the outlet port 240 of the fluid connector to direct a second fluid through the dock 114, where the second fluid is different than the first fluid. The second fluid passage 252 can permit a second medicament to be administered to a patient simultaneously with the delivery of a medicament from the container 112.

It should also be understood that the second fluid passage 252 can be configured to intersect the fluid passage between the first inlet port 238 and the outlet port 240 of the fluid connector, or the second fluid passage 252 can extend to a second fluid outlet of the dock 114. In some embodiments, the second inlet port 250 is a portion of an IV set. The second inlet port 250 can also comprise a luer connector and or a needleless connector.

Figure 9:
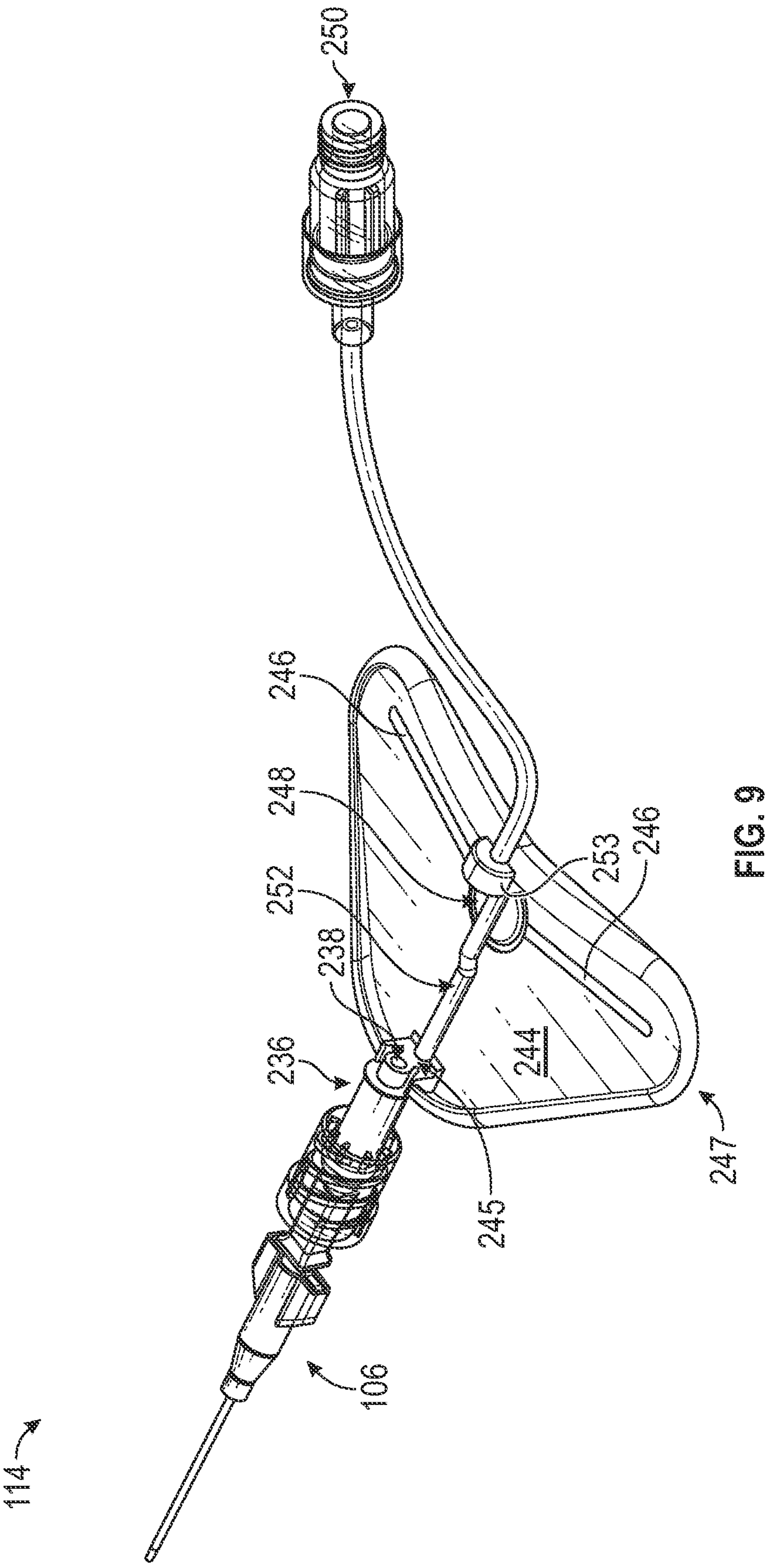
FIG. 9 illustrates a top perspective view of a dock for an activatable medicament delivery container, in accordance with aspects of the present disclosure.

FIG. 9, the dock 114 is illustrated having a top surface 244 with a conductive material forming a portion of an electrical circuit 246. The dock 114 also includes a battery receptacle 248 coupled with the electrical circuit. A bottom surface 247 of the dock can include an adhesive adapted to secure the dock 114 to the skin of a patient to secure the assembly to the patient.

The portion of the electrical circuit 246 on the dock is arranged so that a complete circuit is formed when the container 112 is engaged against the top surface 244 of the dock. In some aspects of the present disclosure, the container comprises another portion of an electrical circuit configured to engage against the portion of the electrical circuit 246 on the dock and activate the container 112. In some embodiments, the electrical circuit can be complete by any means, including moving a switch, removing a tab, or sending a signal.

Figure 10A:
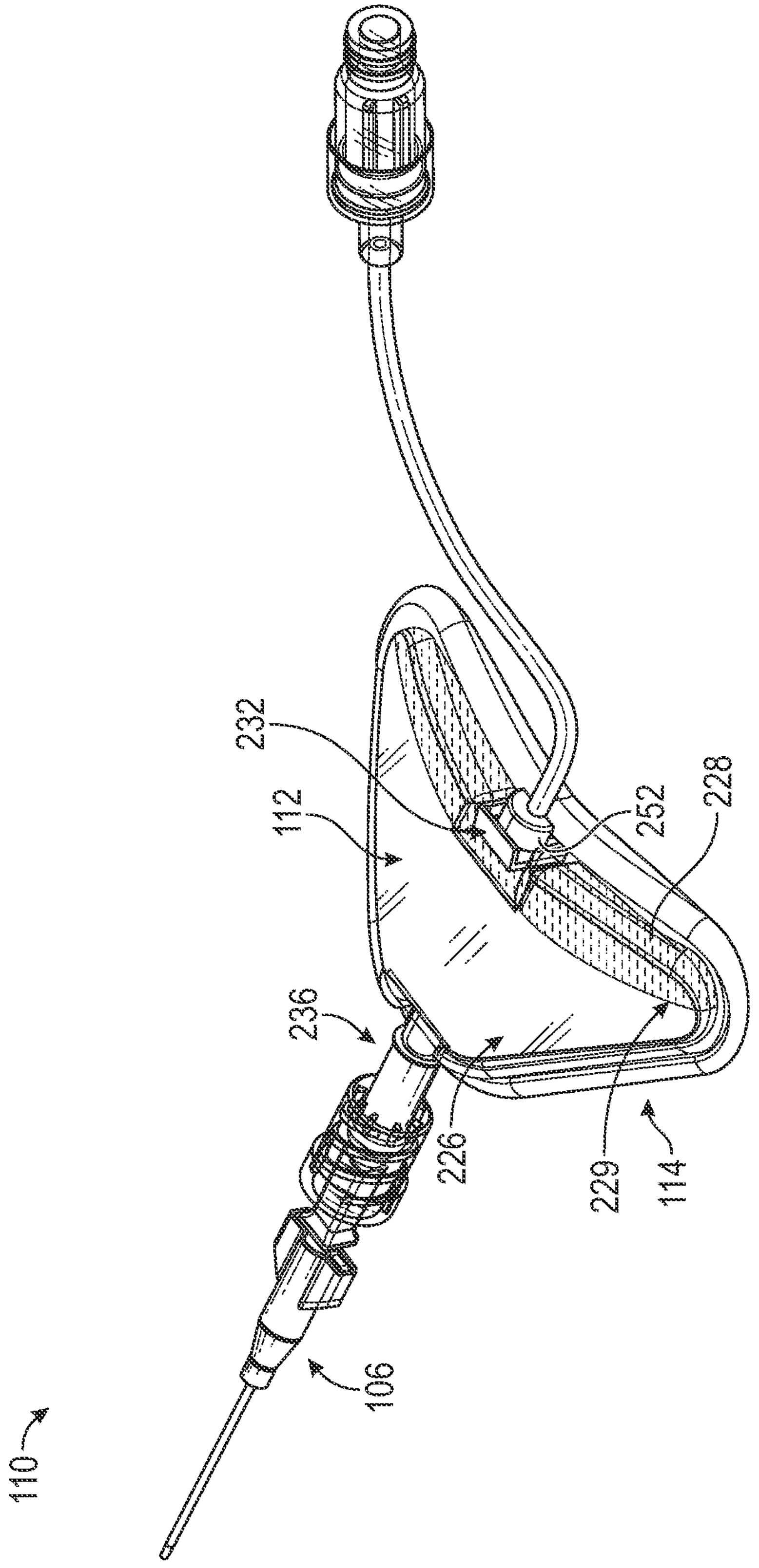
FIGS. 10A-10C illustrate top perspective views of the medicament delivery assembly of FIG. 8, in accordance with aspects of the present disclosure.
Figure 10B:
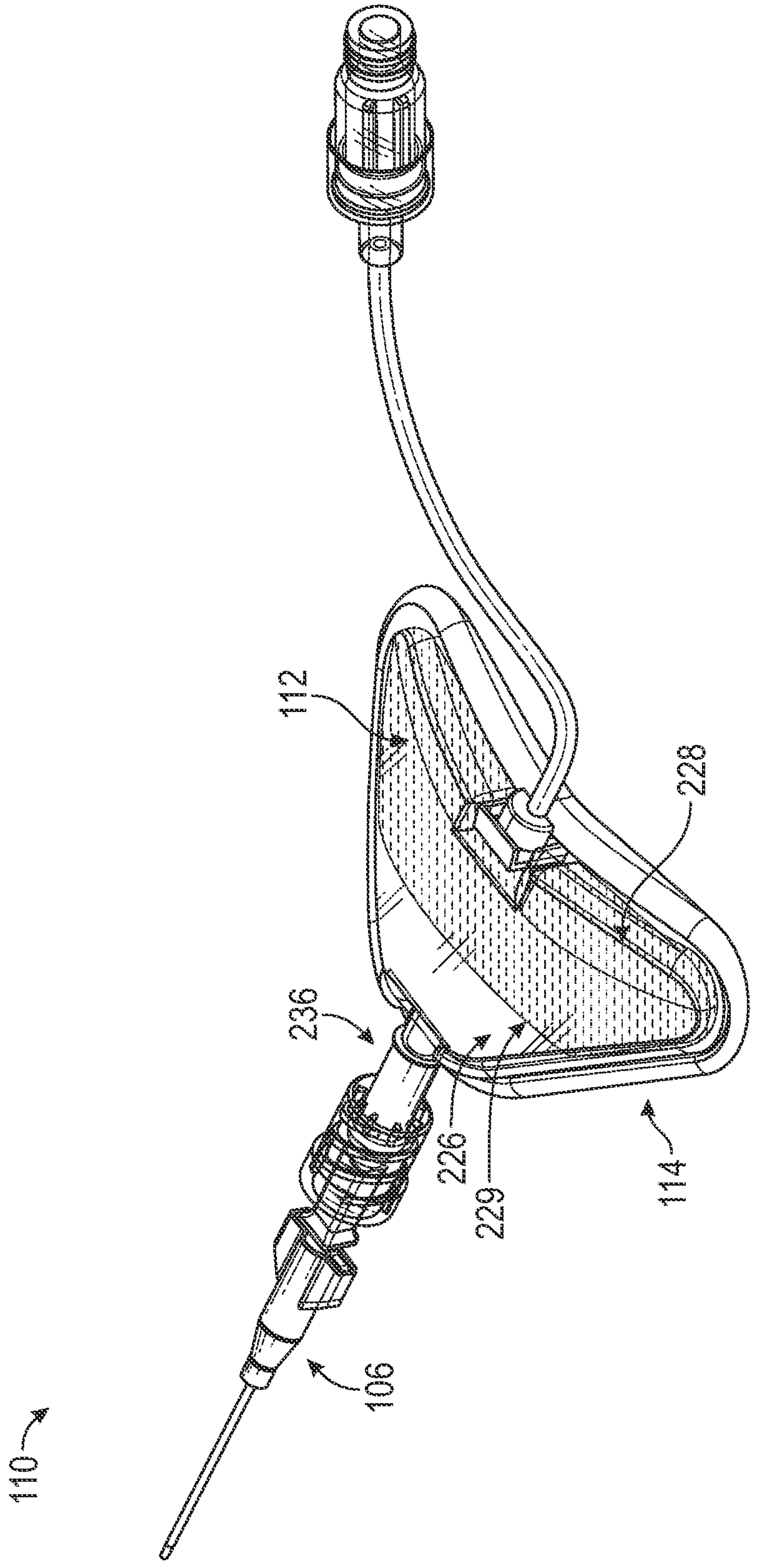
Figure 10C:
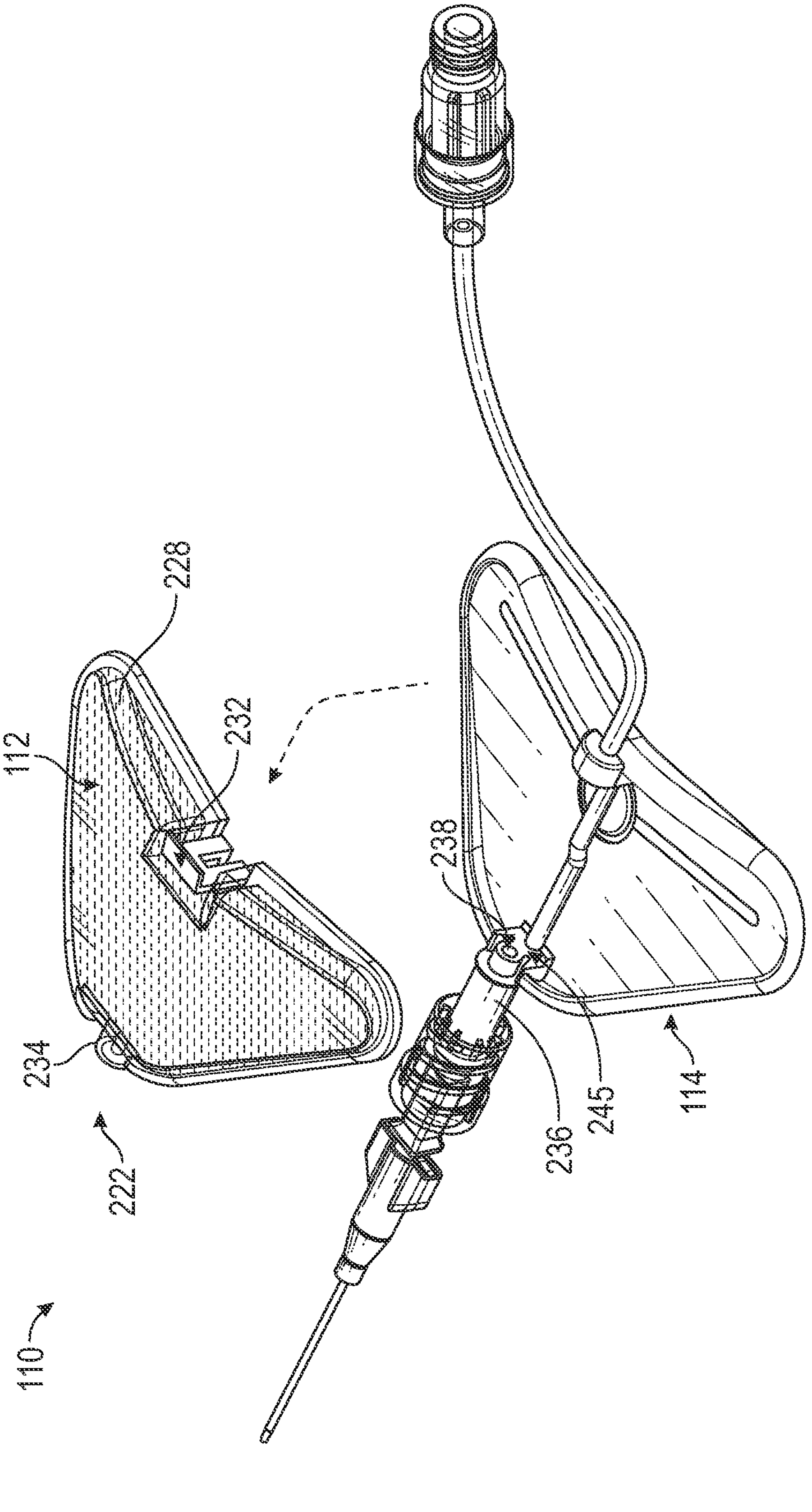

FIGS. 10A, 10B, and 10C illustrate a container 112 coupled with a dock 114 to form an activatable medicament delivery container assembly 110, an activated container 112 that has ejected a medicament, and removal of the container in which the medicament has been ejected, respectively.

When the container 112 is coupled with the dock 114, as illustrated in FIG. 10A, the bottom surface of the container is engaged against the top surface 244 of the dock, the protrusion 234 extends into a channel 245 adjacent to the fluid connector 236, and the tab 232 is engaged against a wall 253 of the dock 114. In some aspects of the present disclosure, the tab engages against the dock 114 and is biased toward the container 112 to permit the container 112 to be moved toward the top surface 244 of the dock. The force of the tab 232 against the dock 114, and the position of protrusion 234 of the container within the channel of the dock, resists movement of the container 112 away from the dock 114.

When the container 112 is activated, as illustrated in FIGS. 10A and 10B, the expansion chamber 228 expands, which displaces a pressure membrane 229 between the medicament chamber 226 and the expansion chamber 228. As the expansion chamber 228 expands, the pressure membrane 229 moves further toward the medicament chamber 226, to cause a pressure within the medicament chamber 226 to increase, thereby ejecting a medicament from the medicament chamber 226 through the fluid connector 236 of the dock The container 112 can be separated from the dock 114 at any time, such as when all of the medicament has been ejected from the container 112 or when a different container is to be coupled with the dock 114, as illustrated in FIG. 10C. To separate the container 112 from the dock 114, the tab 232 is moved or biased away from the wall 253 of the dock 114, and the container 112 can be lifted away from the dock 114 to remove the protrusion 234 from the channel 245 and decouple the medicament port 222 from the first inlet port 238.

In some embodiments of the present disclosure, the fluid connector 236 comprises a valve configured to obstruct the fluid passage of the fluid connector when the valve is in a sealed position. When the valve is in a sealed position, such as when a container 112 is not coupled with the dock 114, a tip of the valve obstructs the first inlet port 238 of the fluid passage. When a container 112 is coupled with a dock 114, the medicament port 222 can move the valve to an unsealed position so that a fluid can move through the fluid connector 236.

After all of the medicament has been ejected from the container 112, or when a different container is to be coupled with the dock 114, a caregiver can remove the container 112 and leave the dock 114 coupled with the patient. If another container 112 is to be coupled to the dock 114, the first inlet port 238 can be disinfected, such as by using a disinfectant-soaked swab, and another container 112 can be coupled to the dock 114.

ILLUSTRATION OF SUBJECT TECHNOLOGY AS CLAUSES

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. An activatable medicament delivery container comprising: a body comprising an inner surface defining a medicament chamber, an expansion chamber, and an activation chamber; a medicament port forming a passage fluidly coupled with the medicament chamber; a pressure membrane that fluidly separates medicament chamber and the expansion chamber; and a breakable membrane comprising a first configuration wherein the breakable membrane fluidly separates the expansion chamber and the activation chamber, and a second configuration wherein the breakable membrane forms a passage between the expansion chamber and the activation chamber; wherein, when the breakable membrane is in the second configuration, an activator material within the activation chamber can contact an expandable material within the expansion chamber through the passage, such that a volume of the expansion chamber increases, thereby displacing a pressure membrane toward the medicament chamber to increase a pressure therein.

Clause 2. The activatable medicament delivery container of Clause 1, wherein, when a pressure increases within the medicament chamber, a medicament is directed out of the medicament chamber through the medicament port.

Clause 3. The activatable medicament delivery container of Clause 1, wherein the body comprises a first activation chamber and a second activation chamber, and wherein the second activation chamber is fluidly separated from the first activation chamber.

Clause 4. The activatable medicament delivery container of Clause 3, wherein the first activation chamber comprises a first volume, and the second activation chamber comprises a second that is a different volume than the first volume.

Clause 5. The activatable medicament delivery container of Clause 3, wherein the first activation chamber comprises a first volume of activator material, and the second activation chamber comprises a second volume of activator material that is a different volume than the first volume of activator material.

Clause 6. The activatable medicament delivery container of Clause 1, wherein the pressure membrane comprises a surface area that is larger than an area in which the medicament chamber and the pressure chamber are intersected by the pressure membrane.

Clause 7. The activatable medicament delivery container of Clause 1, wherein the pressure membrane comprises a stretchable material, such that the pressure membrane can have a first surface area in a first configuration and stretch to have a second surface area in a second configuration, wherein the second surface area is larger than the first surface area.

Clause 8. The activatable medicament delivery container of Clause 7, wherein the pressure membrane can stretch in any of a length and a width thereof.

Clause 9. The activatable medicament delivery container of Clause 1, wherein the pressure membrane and the breakable membrane are contiguous.

Clause 10. The activatable medicament delivery container of Clause 1, wherein the expansion chamber comprises an expandable material, the expandable material comprising an expandable polymer.

Clause 11. The activatable medicament delivery container of Clause 1, wherein the activation chamber comprises an activation material, the activation material comprising a water.

Clause 12. A method of delivering a medicament from an activatable medicament delivery container, the method comprising causing a breakable membrane, which fluidly separates an expansion chamber from an activation chamber, to break such a passage is formed between the expansion chamber and the activation chamber, and an activator material within the activation chamber contacts an expandable material within the expansion chamber through the passage, wherein, contact between the activator material and the expandable material cause a volume of the expansion chamber to increase such that a pressure membrane fluidly separating a medicament chamber from the expansion chamber is displaced toward the medicament chamber, thereby increasing a pressure within the medicament chamber and directing a medicament out of the medicament chamber through a medicament port.

Clause 13. The method of Clause 12, wherein breaking the breakable membrane comprises any of squeezing, compressing, and biasing the activation chamber.

Clause 14. The method of Clause 12, comprising directing the medicament out of the medicament chamber at a first rate by breaking the breakable membrane of a first activation chamber.

Clause 15. The method of Clause 14, comprising directing the medicament out of the medicament chamber at a second rate that is larger than the first rate, by breaking the breakable membrane of the first activation chamber and a breakable membrane of a second activation chamber.

Clause 16. An activatable medicament delivery container comprising: a body comprising an inner surface defining a first chamber, a second chamber, and a third chamber; a medicament port forming a passage fluidly coupled with the first chamber; and a breakable membrane comprising a first configuration wherein the breakable membrane fluidly separates the second chamber and third chambers, and a second configuration wherein the breakable membrane forms a passage between the second chamber and third chambers; wherein, when the breakable membrane is in the second configuration, an activator material within the third chamber can contact an expandable material within the second chamber through the passage, such that a volume of the second chamber increases, thereby displacing a pressure membrane toward the first chamber to increase a pressure within the first chamber.

Clause 17. An activatable medicament delivery assembly comprising: an activatable medicament delivery container comprising an inner surface defining a medicament chamber, an expansion chamber, and a medicament port forming a passage fluidly coupled with the medicament chamber; and a dock comprising a fluid connector, wherein, when the container is coupled with the dock, the medicament port is fluidly coupled with a first inlet port of the fluid connector; wherein, the container is activatable such that an expandable material within the expansion chamber increases a volume of the expansion chamber, thereby displacing a pressure membrane toward the medicament chamber to increase a pressure in the medicament chamber and direct a medicament out of the medicament port and through the fluid connector.

Clause 18. The activatable medicament delivery assembly of Clause 17, wherein the fluid connector comprises a valve having a valve tip configured to obstruct the fluid connector when the valve is in a sealed position.

Clause 19. The activatable medicament delivery assembly of Clause 18, wherein the valve tip and a portion of the dock forming the fluid connector comprise a flat surface the valve is in a sealed position.

Clause 20. The activatable medicament delivery assembly of Clause 17, wherein the fluid connector comprises a second inlet port, an outlet port, a first fluid passage that extends from the first inlet port to the outlet port, and a second fluid passage that extends from the second inlet port to the outlet port.

Clause 21. The activatable medicament delivery assembly of Clause 20, wherein the outlet port comprises a luer connector.

Clause 22. The activatable medicament delivery assembly of Clause 20, wherein the outlet port comprises a syringe.

Clause 23. The activatable medicament delivery assembly of Clause 20, wherein the second inlet port comprises a luer connector.

Clause 24. The activatable medicament delivery assembly of Clause 17, wherein the dock comprises an electrical contact, such that, when the container is coupled with the dock, an electrical current can move between the container and the dock to activate the container.

Clause 25. The activatable medicament delivery assembly of Clause 24, wherein the dock comprises a battery configured to direct the electrical current through the electrical contact.

Clause 26. The activatable medicament delivery assembly of Clause 17, wherein any of the dock and the container comprises a tab configured to engage against the other of the dock and container to resist movement of the container away from the dock when the container is coupled with the dock.

Clause 27. The activatable medicament delivery assembly of Clause 17, wherein the container comprises an activation chamber and a breakable membrane, and wherein, the breakable membrane fluidly separates the activation chamber from the expansion chamber, and when the container is activated, a passage is formed through a breakable membrane between the activation chamber and the expansion chamber.

Clause 28. The activatable medicament delivery assembly of Clause 27, wherein, when the container is coupled with the dock, the container is activated, such that an activator material within the activation chamber can contact the expandable material through the passage of the breakable membrane.

Clause 29. The activatable medicament delivery assembly of Clause 27, wherein, the container is activated, such that an activator material within the activation chamber can contact the expandable material through the passage of the breakable membrane after the container is coupled with the dock.

Clause 30. The activatable medicament delivery assembly of Clause 17, wherein the dock comprises a top surface and a bottom surface, and wherein the top surface is configured to engage against the container, and the bottom surface is configured to engage against skin of a patient.

Clause 31. The activatable medicament delivery assembly of Clause 30, wherein at least a portion of the bottom surface of the dock comprises an adhesive adapted to secure the dock to the skin.

Clause 32. The activatable medicament delivery assembly of Clause 30, wherein the dock comprises a height between the top and bottom surfaces, and a width that is transverse, relative to the height, and wherein the with is larger than the height.

Clause 33. A method of delivering a medicament from an medicament delivery assembly, the method comprising: coupling an activatable medicament delivery container to a dock so that a medicament port of the container is fluidly coupled with a first inlet port of a fluid connector of the dock; and activating the container such that an expandable material within an expansion chamber of the container increases a volume of the expansion chamber, thereby displacing a pressure membrane, fluidly separating the expansion chamber from a medicament chamber of the container, toward the medicament chamber to increase a pressure in the medicament chamber and direct a medicament out of the medicament port and through the fluid connector.

Clause 34. The method of Clause 33, wherein the medicament comprises saline.

Clause 35. The method of Clause 33, comprising coupling an outlet port of the fluid connector to a catheter.

Clause 36. The method of Clause 33, comprising adhering the dock to a patient's skin.

Clause 37. The method of Clause 33, comprising coupling an outlet port of the fluid connector a needle of a syringe.

Clause 38. The method of Clause 33, comprising, directing a fluid through a second inlet port of the fluid connector, wherein the second inlet port is fluidly coupled to an outlet port of the fluid connector.

Clause 39. The method of Clause 33, comprising disinfecting the fluid connector of the dock before coupling the container to the dock.

Clause 40. The method of Clause 33, wherein coupling the container to the dock comprises engaging a tab of any of the dock and the container against the other of the dock and container to resist movement of the container away from the dock.

Clause 41. The method of Clause 33, wherein activating the container comprises completing an electrical circuit between the dock and the container.

Clause 42. The method of Clause 33, wherein activating the container comprises forming a passage through a breakable membrane between an activation chamber and the expansion chamber, such that an activator material within the activation chamber can contact the expandable material through the passage of the breakable membrane.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An activatable medicament delivery container comprising:

a body comprising an inner surface defining a medicament chamber, an expansion chamber, and a first activation chamber and a second activation chamber, wherein the second activation chamber is fluidly separated from the first activation chamber;

a medicament port forming a passage fluidly coupled with the medicament chamber;

a pressure membrane that fluidly separates medicament chamber and the expansion chamber; and a breakable membrane comprising a first configuration wherein the breakable membrane fluidly separates the expansion chamber from the first and second activation chambers, and a second configuration wherein the breakable membrane forms a passage between the expansion chamber and any of the first and second activation chambers;

wherein, when the breakable membrane is in the second configuration, an activator material within the first and/or second activation chamber can contact an expandable material within the expansion chamber through the passage, such that a volume of the expansion chamber increases, thereby displacing a pressure membrane toward the medicament chamber to increase a pressure therein.

2. The activatable medicament delivery container of claim 1, wherein, when a pressure increases within the medicament chamber, a medicament is directed out of the medicament chamber through the medicament port.

3. The activatable medicament delivery container of claim 1, wherein the first activation chamber comprises a first volume, and the second activation chamber comprises a second volume that is a different volume than the first volume.

4. The activatable medicament delivery container of claim 1, wherein the first activation chamber comprises a first volume of activator material, and the second activation chamber comprises a second volume of activator material that is a different volume than the first volume of activator material.

5. The activatable medicament delivery container of claim 1, wherein the pressure membrane comprises a surface area that is larger than an area in which the medicament chamber and the expansion chamber are intersected by the pressure membrane.

6. The activatable medicament delivery container of claim 1, wherein the pressure membrane comprises a stretchable material, such that the pressure membrane can have a first surface area in a first configuration and stretch to have a second surface area in a second configuration, wherein the second surface area is larger than the first surface area.

7. The activatable medicament delivery container of claim 1, wherein the pressure membrane and the breakable membrane are contiguous.

8. The activatable medicament delivery container of claim 1, wherein the expansion chamber comprises an expandable material, the expandable material comprising an expandable polymer.

9. The activatable medicament delivery container of claim 1, wherein each of the first and second activation chambers comprise an activation material, the activation material comprising a water.

10. The activatable medicament delivery container of claim 1, wherein the breakable membrane comprises a channel that extends into the breakable membrane.

11. The activatable medicament delivery container of claim 1, wherein the breakable membrane comprises a first channel that extends into the breakable membrane in direction from the expansion chamber toward the first activation chamber.

12. The activatable medicament delivery container of claim 11, wherein the breakable membrane comprises a second channel that extends into the breakable membrane in direction from the expansion chamber toward the second activation chamber.

13. A method of delivering a medicament from an activatable medicament delivery container, the method comprising causing a first breakable membrane, which fluidly separates an expansion chamber from a first activation chamber, to break such that a passage is formed between the expansion chamber and the first activation chamber, and an activator material within the first activation chamber contacts an expandable material within the expansion chamber through the passage, wherein, contact between the activator material and the expandable material cause a first volume of the expansion chamber to increase such that a pressure membrane fluidly separating a medicament chamber from the expansion chamber is displaced toward the medicament chamber, thereby increasing a pressure within the medicament chamber and directing a medicament out of the medicament chamber at a first rate through a medicament port, and directing the medicament out of the medicament chamber at a second rate that is larger than the first rate, by breaking a second breakable membrane of a second activation chamber.

14. The method of claim 13, wherein breaking any of the first and second breakable membranes comprises any of squeezing, compressing, and biasing any of the first and second activation chambers.

15. The method of claim 13, wherein directing the medicament out of the medicament chamber at a second rate comprises breaking the second breakable membrane of a second activation chamber, wherein the second activation chamber comprises a second volume that is a different volume than the first volume.

16. The method of claim 13, wherein directing a medicament out of the medicament chamber at a first rate and directing the medicament out of the medicament chamber at a second rate comprises simultaneously breaking the first breakable membrane and the second breakable membrane.

17. The method of claim 13, wherein directing a medicament out of the medicament chamber at a first rate and directing the medicament out of the medicament chamber at a second rate comprises breaking the second breakable membrane after breaking the first breakable membrane.

* * * * *